United States Patent [19]
Pariza et al.

[11] Patent Number: 5,837,733
[45] Date of Patent: Nov. 17, 1998

[54] METHOD FOR REDUCING SECETION OF APOLIPOPROTEIN B IN ANIMALS BY ADMINISTERING CONJUGATED LINOLEIC ACID

[75] Inventors: Michael W. Pariza, Madison, Wis.; Kisun N. Lee, Seoul, Rep. of Korea

[73] Assignee: Wisconsin Alumni Research Foundation, Madison, Wis.

[21] Appl. No.: 805,486

[22] Filed: Feb. 26, 1997

[51] Int. Cl.⁶ .................................................. A61K 31/20
[52] U.S. Cl. ............................................................ 514/560
[58] Field of Search ................................... 514/549, 560

[56] References Cited

U.S. PATENT DOCUMENTS 5,290,684  3/1994  Kelly .
5,550,034  8/1996  Teng et al. .

OTHER PUBLICATIONS

Haumann, Barbara F., "Conjugated linoleic acid offers research promise," *Inform*, 7–2:152–159 (1996).

Kisun, N. Lee, et al., "Conjugated linoleic acid and atherosclerosis in rabbits," *Atherosclerosis*, 108:19–25 (1994).

Nicolosi, Robert J., et al., "Dietary Conjugated Linoleic Acid Reduces Aortic Fatty Streak Formation Greater Than Linoleic Acid in Hypercholesterolemic Hamsters," Abstract, *The FASEB Journal*, 10–3:A477 (1996).

Nicolosi, Robert J., et al., "Effect of Feeding Diets Enriched in Conjugated Linoleic Acid on Lipoproteins and Aerotic Atherogenesis in Hamsters," *Circulation* 88 Suppl. 2458 (1993).

*Primary Examiner*—Raymond Henley, III
*Attorney, Agent, or Firm*—Quarles & Brady

[57] ABSTRACT

A method of reducing apolipoprotein B secretion comprises making available to animal cells an amount of conjugated linoleic acid effective to reduce apolipoprotein B secretion from the cells. A related method comprises administering to an animal a safe and effective amount of a conjugated linoleic acid to reduce apolipoprotein B secretion into the animal's bloodstream.

10 Claims, 3 Drawing Sheets

METHOD FOR REDUCING SECETION OF APOLIPOPROTEIN B IN ANIMALS BY ADMINISTERING CONJUGATED LINOLEIC ACID

BACKGROUND OF THE INVENTION

The present invention generally relates to animal nutrition. More particularly, it relates to a method of reducing secretion of Apolipoprotein B from animal cells.

In today's health conscious society there is a great interest in blood cholesterol levels. Blood cholesterol is classified according to the density of its associated lipoproteins. The lipoprotein classes include very low density lipoproteins (VLDL), low density lipoproteins (LDL) and high density lipoproteins (HDL). The corresponding cholesterol classes are VLDL-, LDL-, and HDL-cholesterol, respectively.

Apolipoproteins AI (apo AI) and apolipoprotein B (apo B) are proteins that associate specifically with particular blood lipids. Apo AI associates specifically with HDL-cholesterol, the so-called "good" cholesterol. Apo B associates with VLDL-cholesterol and LDL-cholesterol, the so-called "bad" cholesterol. It is thought that Apo B plays a role in maintaining VLDL- and LDL-cholesterol in the bloodstream. It is thought that by reducing secretion of apo B into the bloodstream, the amount of bad cholesterol retained in the bloodstream can also be reduced.

The retardation of atherosclerosis in intact animals by conjugated linoleic acid appears to be due in part to the changes in lipoprotein metabolism (decreasing LDL cholesterol and increasing HDL cholesterol) (Lee, et al., "Conjugated linoleic acid and atherosclerosis in rabbits," *Atherosclerosis* 108:19–25 (1994)). The ability to reduce LDL levels in intact animals fed conjugated linoleic acids has been reported (Lee, et al., "Conjugated Linoleic Acid and Atherosclerosis in Rabbits," *Atherosclerosis* 108:19–25 (1994); Nicolosi, et al., "Effect of Feeding Diets Enriched in Conjugated Linoleic Acid on Lipoproteins and Aerotic Atherogenesis in Hamsters," *Circulation* 88 Suppl.: 2458 (1993).) Nicolosi and Laitinen, report that conjugated linoleic acid had insignificant effect on plasma lipids and lipoprotein cholesterol, but did bring about a significant 45% reduction in aortic fatty streak formation after feeding to hamsters. FASEB Journal Abstract No. 2751, page A477, Apr. 1996.

The human liver plays a central role in lipid and lipoprotein metabolism. A cultured human hepatoma cell line that exhibits a lipid metabolism pattern similar to normal liver parenchymal cells is Hep G2 (ATCC Accession No. HB 8065). Hep G2 cells are widely used in laboratory systems designed to model human liver cell function. Hep G2 cells retain the capacity to synthesize and secrete lipoprotein fractions (Javitt, N.B., "Hep G2 cells as a resource for metabolic studies: lipoprotein, cholesterol, and bile acids," *FASEB J.* 4:161–168 (1990)), especially triglyceride-rich lipoprotein with the density of LDL, the apolipoprotein content of which is almost exclusively apo B (Ellsworth, et al., "Very low and low density lipoprotein synthesis and secretion by human hepatoma cell line Hep G2: effect of free fatty acid," *J. Lipid Res.* 27:858:874 (1986), Thrift, et al., "Characterization of Lipoproteins Produced by the Human Liver Cell Line Hep G2 Under Defined Conditions," *J. Lipid Res.* 27:236–250 (1986).). A 100 kD apo B is the sole apo B species secreted by the human liver and is also the only apo B species synthesized and secreted by cultured human Hep G2 cells. Rash, et al., "Lipoprotein Apolipoprotein Synthesis by Human Hepatoma Cells in Culture, " *Biochim. Biophys. Acta* 666:294–298 (1981). Apo B secretion is translationally regulated.

There is an obvious need for a safe and effective method of reducing the levels of Apolipoprotein B secreted from animal cells and, hence, blood cholesterol levels.

BRIEF SUMMARY OF THE INVENTION

It is an object of the present invention to disclose a method for reducing secretion of Apolipoprotein B from animal cells.

We have discovered a method for reducing Apolipoprotein B from animal cells which comprises making available to the cells a compound selected from 9,11-octadecadienoic acid; 10,12-octadecadienoic acid; mixtures thereof; active esters and non-toxic salts thereof (CLA), which is effective to reduce Apolipoprotein B secretion from the cells.

In a second aspect, the invention is a method for reducing secretion of Apolipoprotein B from animal cells in an animal which comprises administering to an animal a safe amount of a compound selected from 9,11-octadecadienoic acid; 10,12-octadecadienoic acid; mixtures thereof; active esters and non-toxic salts thereof (CLA), which is effective to reduce Apolipoprotein B secretion into the bloodstream of the animal.

It will be apparent to those skilled in the art that the aforementioned objects and other advantages may be achieved by the practice of the present invention.

DETAILED DESCRIPTION OF THE INVENTION

Figure 1:
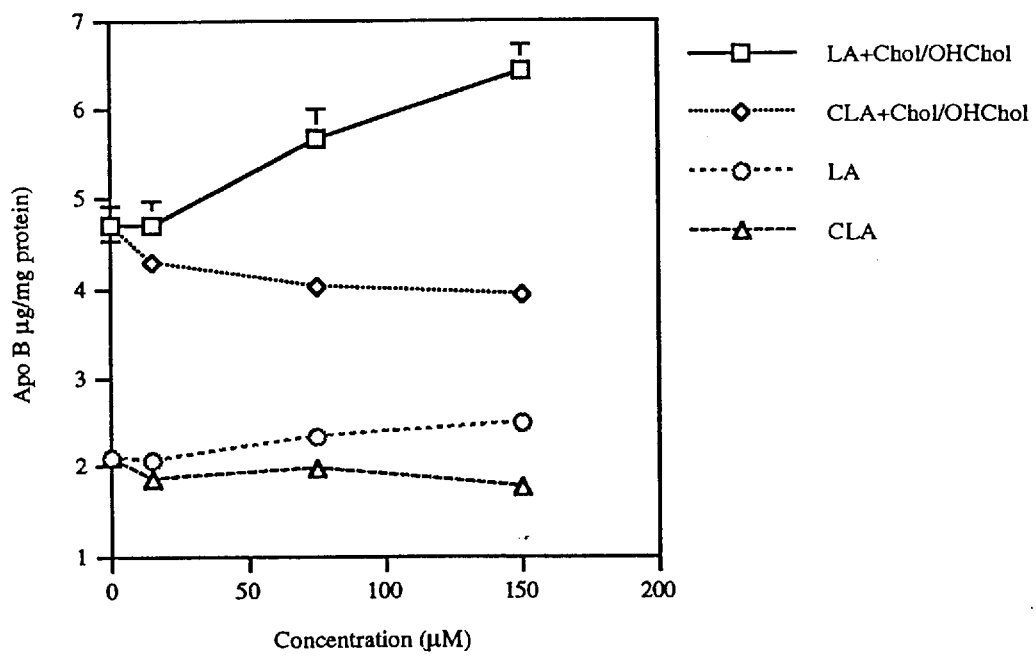
FIG. 1 shows the effect of CLA on apo B secretion in Hep G2 cells incubated with or without Chol/OH-Chol. The differences in the apo B content between LA-treated and CLA-treated cells are significant (regression analysis, p<0.001). Data represent mean±SEM.

In one preferred embodiment of the method of the present invention the safe and effective amount of conjugated linoleic acid (CLA), which are fatty acids selected from 9,11-octadecadienoic acid; 10,12-octadecadienoic acid; mixtures thereof; active esters and non-toxic salts thereof is made available to animal cells from which it is desired to reduce Apolipoprotein B secretion. The non-toxic salts of the free acids may be made by reacting the free acids with a non-toxic base.

In a second embodiment, an amount of CLA is added to an animal's diet in an amount effective to reduce secretion of Apo B from an animal's cells into the bloodstream of the animal. The amount of CLA to be added to the animal's diet will vary with the species and size of the animal. However, since the conjugated linoleic acids are natural food ingredients and relatively non-toxic, the amount which can be administered is not critical as long as it is enough to be effective.

The practice of the present invention is further illustrated by the examples which follow. All papers cited in the Examples are incorporated herein by reference.

TABLE OF ABBREVIATIONS

| | |
|---|---|
| Apo AI | apolipoprotein AI |
| Apo B | apolipoprotein B |
| BSA | bovine serum albumin |
| CE | cholesterol ester |
| Chol/OH-Chol | cholesterol and 25-OH cholesterol |
| CLA | conjugated linoleic acid, as defined herein |
| DHA | Docosahexaenoic acid C22:6 |
| DiI | 3,3'-dioctadecylindocarbocyanine |
| DMEM | Dulbecco's Modified Eagle's Medium |
| DMSO | dimethyl sulfoxide |
| ELISA | enzyme linked immunosorbent assay |
| EPA | Eicosapentaenoic acid C20:5 |
| FBS | fetal bovine serum |
| HDL | high density lipoprotein |
| LA | linoleic acid |
| LDL | low density lipoprotein |
| PBS | phosphate buffered saline |
| TG | triglyceride |
| VLDL | very low density lipoprotein |

Conjugated Linoleic Acid (CLA)

CLA was prepared from linoleic acid by alkali isomerization as described by Chin, et al., Food Composition and Analysis 5:185–197 (1992). The purity of CLA exceeded 95%, and consisted of two major and several minor isomers. The two major isomers were c9,t11-CLA (42%) and t10, c12-CLA (44%).

Cell Culture

Hep G2 cells (ATCC HB 8065) were obtained from ATCC. Cell stocks were maintained in DMEM with non-essential amino acids containing antibiotics with 10% FBS, and incubated at 37° C. in a humidified atmosphere of 95% air, 5% $CO_2$. Subcultures for the experiments were obtained from stock monolayers using trypsin. The medium was changed every 2 or 3 days. For the experiments, confluent monolayers were washed several times with PBS and incubated with first with serum-free DMEM for 24 hours and then with followed by albumin-containing DMEM, with or without corresponding fatty acids (LA or CLA). Fatty acid was complexed with fatty acid-free BSA in a 2:1 molar ratio according to Mahoney, et al. (Mahoney, et al., "Response of endocytosis to altered fatty acyl composition of macrophage phospholipids," Pro. Natl. Sci. USA 74:4895–4899 (1977)). Unless otherwise stated, cell monolayers were washed and harvested after incubation for 24 hours in an experimental medium. Cytotoxicity was assessed by trypan blue exclusion and by MTT-dye (dimethylthiazol diphenyltetrazolium bromide) reduction (Plumb, et al., "Effects of the pH dependence of 3-(4,5-dimethylthiazol-2-yl)-2,5-diphenyl-tetrazolium bromide-formazan absorption on chemosensitivity determination by a novel tetrazolium-based assay," Cancer Res. 49:4435–4440 (1989)).

Lipid Analysis

After a 24 hour fatty acid treatment, cell monolayers were washed and harvested. After centrifugation, cell pellets were washed and resuspended. Aliquots of cell suspensions were sampled for protein concentration (Gogstad, et al., "Measurement of protein in cell suspensions using the coomassie brilliant blue dye-binding assay," Anal. Biochem. 126:355–359 (1982)). Total lipids were extracted from cell suspensions and from the media with ethyl acetate: acetone (2:1) Slayback, et al., "Quantitative Extraction of Microgram Amounts of Lipid from Cultured Human cells," Anal. Biochem 126:355–359 (1982). The free and esterified cholesterol were measured using enzymatic methods as described previously (Sale, et al., "A sensitive enzymatic assay for determination of cholesterol in lipid extracts," Anal. Biochem. 142:347–350 (1984)). Total triglycerides were also determined enzymatically (Sigma Chemicals Co., St. Louis, Mo.). Fatty acid methyl esters were prepared with 4- HCl/methanol (Luddy, et al., "Direct conversion of lipid components to their fatty acid methyl esters," J. Am. Oil Chem. Soc. 37:447–450 (1960)) and were separated by gas chromatography (Ha, et al., "Newly recognized anticarcinogenic fatty acids: Identification and quantification in natural and processed cheeses," J. Agric. Food. Chem. 37:75–81 (1989)).

Apolipoprotein Apo B Assay

Both unconjugated and peroxidase-conjugated antibodies were purchased from Binding Site (Birmingham, UK). Apo B content was measured by sandwich-type ELISA in cells and media (Hahn, et al., "Enzyme-linked immunosorbent assay to measure apolipoproteins A1 and B secretion by a human hepatic carcinoma cell line (Hep G2), J. Clin. Lab. Anal. 6:182–189 (1992)). Briefly, microtiter plates were coated with capture antibody and subsequently blocked with BSA. Samples or apolipoprotein standards were added to the wells and incubated for 18 hours at 4° C. After washing, peroxidase-conjugated antibody was allowed to bind to the antigen-coated wells for 5 hours followed by extensive washing. Freshly prepared substrate mixture (o-phenylenediamine dihydrochloride) was added to each well and incubated in the dark. The absorbance was measured at 490 nm.

LDL Receptor Activity

The LDL receptor activity was measured using a fluorometric assay with DiI-labeled LDL (DiI-LDL), as described by Stephan and Yurachek (Stephan et al., "Rapid fluorometric assay of LDL receptor activity by DiI-labeled LDL," J. Lipid Res. 34:325–330 (1993)). A stock solution of the fluorescent probe, DiI (Molecular Probes Inc., Eugene, Oreg.), was prepared by dissolving it in DMSO. Subsequently, LDL was labeled with DiI to yield a final ratio of 300 µg DiI to 1 mg LDL protein. The labeled DiI-LDL was dialyzed, filter-sterilized and used for the experiment. To determine the activity of the LDL receptor, cells were incubated with supplemented fatty acids for 6 to 24 hours. Subsequently, cells were incubated with a medium containing 30 µg/ml DiI-LDL at 37° C. for 2 hours. After washing, cell-associated DiI was extracted from the cells using isopropanol for the fluorescence determination to assess LDL receptor activity. Total cell-associated DiI-LDL (µg/mg protein) was used for LDL receptor activity.

Statistical Analysis

Results are expressed as mean±standard error unless otherwise stated. Data were analyzed by the Student's t-test or one-way ANOVA and Tukey's multiple range test. Regression analysis was performed using SPSS. The difference was considered significant if the p value was less than 0.05.

Results

Less Apo B accumulates outside of cells treated with CLA than cells treated with LA. FIG. 1 summarizes apo B accumulation in a culture medium from Hep G2 cells after 24 hours incubation with LA or CLA either in the presence or absence of chol/OH-chol. Regression analysis showed that the apo B content of the medium was significantly increased (p<0.001) by the concentration of LA and was decreased by CLA. Apo B secreted into the culture medium from cells incubated with 150 μM of CLA was significantly (p<0.001) lower than that of controls. In contrast, LA markedly increased apo B accumulation in the culture medium.

|  | μg ApoB/mg protein secreted |
| --- | --- |
| 150 μM LA | 2.50 ± 0.17 |
| 150 μM CLA | 1.76 ± 0.06 |
| Control | 2.11 ± 0.05 |

The effect of LA or CLA on apo B secretion was more evident when Hep G2 cells were incubated in culture medium that contained chol/OH-chol (5 μg/ml cholesterol and 4 μg/ml OH-cholesterol). When Hep G2 cells are exposed to chol/OH-chol, Apo B secretion is more than twice as high as in untreated control cells. In chol/OH-chol-treated cells, LA further increased the level of apo B in the medium by 35% compared to chol/OH-chol-treated controls. On the other hand, CLA diminished the enhancing effect of chol/OH-chol on apo B secretion (FIG. 1).

No statistical difference in cellular apo B was observed among the groups. Cellular apo B levels were not significantly altered by exposure to chol/OH-chol, nor by exposure to CLA or LA.

|  | μg ApoB/mg cellular protein |
| --- | --- |
| +chol/OH-chol | 1.69 ± 0.06 |
| −chol/OH-chol | 1.59 ± 0.16 |
| 150 μM LA | 1.77 ± 0.10 |
| 150 μM CLA | 1.72 ± 0.13 |

Figure 2:
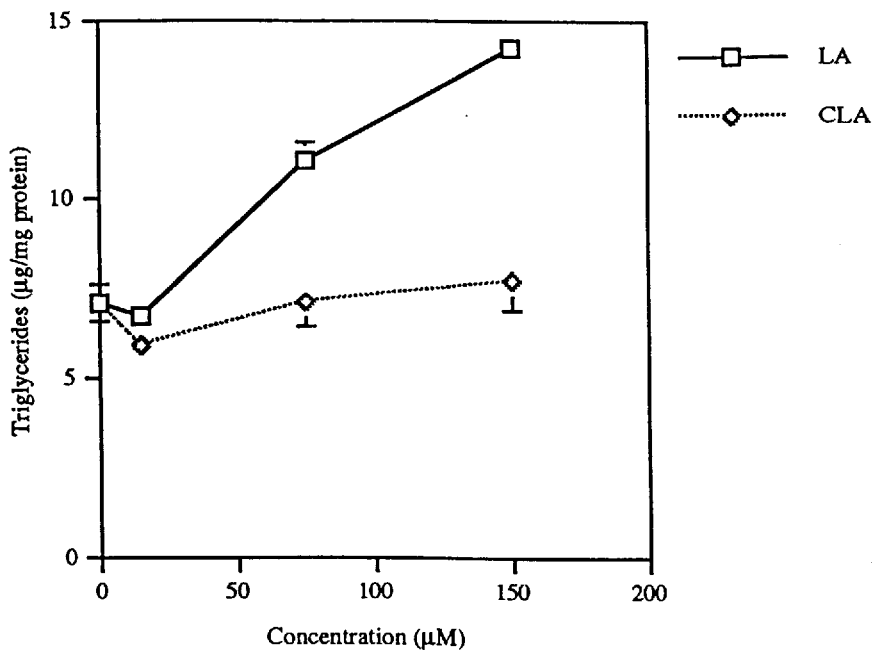
FIG. 2 shows the effect of CLA on triglyceride secretion in Hep G2 cells. The difference between LA and CLA is significant (p<0.001). Data represents mean±SEM.

Since apo B-containing lipoproteins from Hep G2 cells are mostly triglyceride (TG) (Thrift, et al., "Characterization of lipoproteins produced by the human liver cell line, Hep G2, under defined conditions," *J. Lipid Res.* 27:236–250 (1986)), rather than cholesterol ester (CE), which would be typical of normal circulating LDL, TG was measured in the culture medium. CLA also does not increase secretion of triglycerides from cells. FIG. 2 shows TG secretion as a function of LA or CLA concentration. LA significantly increased TG content in the medium, but no difference in secreted TG was observed between control and CLA-supplemented groups.

|  | μg TG/mg secreted protein |
| --- | --- |
| 150 μM LA | 14.2 ± 0.4 |
| 150 μM CLA | 7.7 ± 0.8 |
| Control | 7.1 ± 0.5 |

Although secretion of apo B-containing lipoprotein appeared similar in the control and CLA groups when assessed by the TG content of the culture medium, it is more reliable to measure apo B accumulation in the medium to understand lipoprotein secretion rate in Hep G2 cells. Arrol, et al. (Arrol, et al., "Lipoprotein secretion by the human hepatoma cell line Hep G2: differential rates of accumulation of apolipoprotein B and lipoprotein lipids in tissue culture media in response to albumin, glucose and oleate," *Biochim. Biophys. Acta* 1086:72–80 (1991)) proposed that lipoprotein lipid measurements do not accurately reflect the rate of lipoprotein secretion by Hep G2 cells. The level of apo B in the medium appears to be more stable, and therefore, for studies of the control of lipoprotein secretion by Hep G2 cells, it is more accurate to measure the apo B accumulated in the medium to assess the lipoprotein secretion rate. On this basis, it is believed that LA increased and CLA decreased apo B-containing lipoprotein secretion by Hep G2 cells. Similarly, Wong and Nestel (Wong, et al., "Eicosapentaenoic acid inhibits the secretion of triglycerol and of apoprotein B and the binding of LDL in Hep G2 cells," *Atherosclerosis* 64:139–146 (1987)) have shown that apo B and TG secretions from Hep G2 cells were enhanced by LA, compared to an albumin control, and were inhibited by eicosapentaenoic acid.

Figure 3:
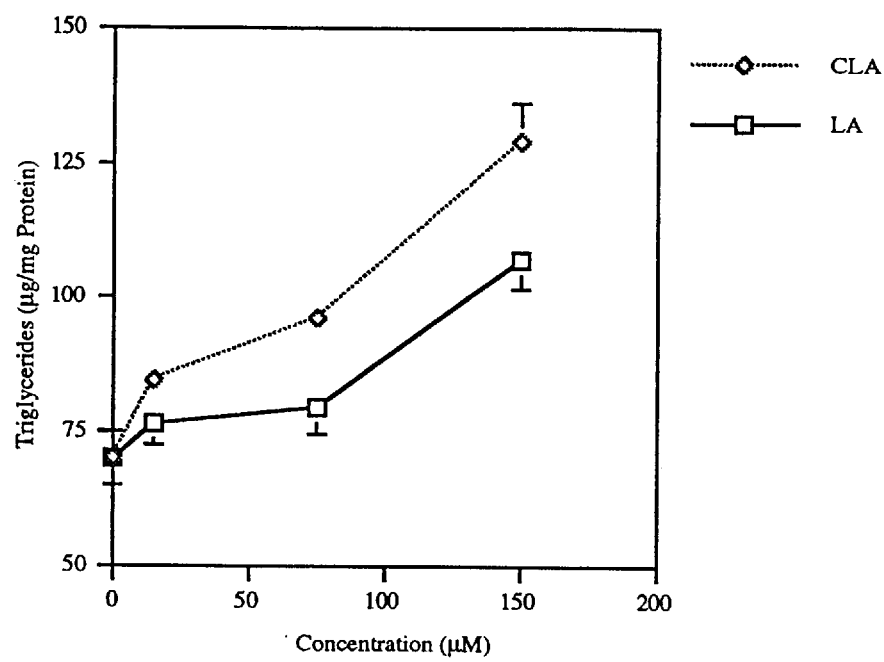
FIG. 3 shows the effect of CLA on cellular content of triglyceride in Hep G2 cells. The difference between CLA and LA is significant (p<0.001). Data represent mean±SEM.

LA and CLA both markedly increased cellular TG as compared to an albumin control (FIG. 3). The cells accumulated even more cellular TG after CLA treatment than after LA treatment.

Chol/OH-chol treatment increased the cellular cholesterol content compared to albumin-treated controls, but neither LA nor CLA significantly altered cellular cholesterol content in the presence or in the absence of chol/OH-chol in the culture medium.

|  | μg chol/mg cellular protein |
| --- | --- |
| +chol/OH-chol | 94.3 ± 5.1 |
| −chol/OH-chol | 40.2 ± 2.4 |

In the absence of chol/OH-chol, neither LA nor CLA significantly altered LDL receptor activity compared to controls. The addition of chol/OH-chol to the culture medium reduced LDL receptor activity by 20%.

|  | LDL receptor activity (24 hours) (μg/mg protein) |
| --- | --- |
| +chol/OH-chol | 7.3 ± 0.2 |
| −chol/OH-chol | 9.7 ± 0.3 |

CLA mitigated the inhibitory effect of chol/OH-chol on LDL receptors at 6 hours (8.6±0.4 μg/mg protein), nonetheless the LDL receptor activity of CLA-treated cells was similar after 24 hours of incubation. On the other hand, LDL receptor activity after 24 hours was significantly decreased if the chol/OH-chol treatment was supplemented with LA (8.7±0.2 μg/mg protein).

A previous report (Byrne, et al., "Control of Hep G2 cell triglycerol and apolipoprotein B synthesis and secretion by polyunsaturated non-esterified fatty acids and insulin," *Biochem J.* 288:101–107 (1992)) demonstrated that there is a significant correlation between the intracellular content of apo B and secreted apo B and TG. However, in our study apo B accumulation in the medium was found to be independent of intracellular apo B content. This finding is consistent with other results which show that in response to fatty acid challenges, apo B secretion is altered over a wide range (Pullinger, et al., "The apoprotein B gene is constitutively expressed in Hep G2 cells: regulation of secretion by oleic acid, albumin, and insulin, and measurement of the mRNA half-life," *J. Lipid Res.* 30:1065–1077 (1989), Wong, et al., "Effects of eicosapentaenoic and docosahexaenoic acids on apoprotein B mRNA and secretion of very low density lipoprotein in Hep G2 cells," *Arteriosclerosis* 9:836–841 (1989)).

The accumulation of intracellular TG in LA or CLA-treated cells seems nonspecific. There are many studies showing that cellular content of TG in Hep G2 cells is increased with other fatty acid supplementation (Ellsworth, et al., supra, Wong, et al., supra, Sorci-Thomas, et al., "Hep G2 cell LDL receptor activity and the accumulation of apolipoprotein B and E in response to docosahexaenoic acid and cholesterol," *J. Lipid Res.* 33:1147–1156 (1992)), but only a small percentage is secreted. It has also been suggested that the intracellular apo B content regulates lipoprotein secretion, whereas the intracellular TG content is not associated with secreted TG or apo B (Byrne, et al., supra). It is therefore likely that, relative to albumin-treated cells, LA and CLA both stimulated apo B-containing lipoprotein synthesis in Hep G2 cells. However, CLA, but not LA, inhibited secretion with the core consisting mostly of TG.

Although some studies indicate that the cellular cholesterol stimulates apo B accumulation in Hep G2 cell culture medium (Carlson, et al., "Effect of 25-hydroxycholesterol and bile acids on the regulation of cholesterol metabolism in Hep G2 cells, *Biochem. J.* 264:241–247 (1989); Dashti, et al., "Regulation of apolipoprotein B gene expression by cholesterol in Hap G2 cells," *Circulation* 82 (Suppl III): 2106 (1990); Fuki, et al., "Effect of cell cholesterol content on apolipoprotein B secretion and LDL receptor activity in the human hepatoma cell line, Hep G2., *"Biochim. Biophys. Acta* 1001:235–238 (1989)), LA, which increased apo B secretion in the present study, was not observed to increase cholesterol content. It seems that apo B secretion increases and LDL receptor activity decreases when a large amount of cellular cholesterol (e.g., the addition of chol/OH-chol to the culture medium) is present. However, an increased cholesterol supply is not necessary to stimulate synthesis and secretion of apo B-containing lipoproteins in Hep G2 cells.

Cholesterol and/or 25-OH cholesterol (chol/OH-chol) have been shown to decrease LDL receptor activity. The LDL receptor activity appeared to be inversely associated with the apo B content in the medium, even though it seemed not to be sensitive to the amount of apo B accumulation in Hep G2 cells. A significant difference in LDL receptor activity was observed only when the difference of apo B content between the groups was greater than 1.5 μg/mg protein. It is likely that the LDL receptor was not saturated since the LDL receptor in Hep G2 cells is abundant. It might be difficult to distinguish a small difference with this analytical method using a fluorescent probe. Additionally, down-regulation of the LDL receptor after internalization of LDL may be low in Hep G2 cells. Thus, the interaction of Hep G2 cells with LDL qualitatively, but not quantitatively, mimics LDL metabolism in vivo (Javitt, et al., supra).

Hep G2 cells are accepted as a good model for human hepatocyte function. Fatty acid-mediated changes in apo B-containing lipoprotein synthesis or secretion have been studied in Hep G2 cells (Arrol, et al., supra, Wong, et al., supra, Byrne, et al., supra, Pullinger, et al., supra). Oleic acid (C18:1), most extensively studied in Hep G2 cells, increases apo B accumulation in a culture medium. Fish oil-derived n-3 fatty acids such as eicosapentaenoic acid (EPA, C20:5) and docosahexaenoic acid (DHA, C22:6) have been shown to decrease (Wong, et al., supra, Byrne, et al., supra) or to increase (Sorci-Thomas, et al., supra) apo B-containing lipoprotein secretion in Hep G2 cells. Although the reasons for the differences in apo B secretion in response to n-3 fatty acids are not apparent, they may be related to differences in the cell culture conditions including concentration of these fatty acids, incubation periods, and confluency.

The observed reduction in Apo B secretion in Hep G2 cells provides strong motivation to carry out additional experiments, first in small mammalian animal systems such as the mouse, hamster or rabbit and then in humans.

In such animals or in humans, free linoleic acid is administered to an animal which can convert the linoleic acid into CLA or which modulates the level of CLA in the body of an animal or a human. The linoleic acid is converted to CLA in the animal, probably by microorganisms in the animal's gastrointestinal system (S. F. Chin, J. M. Storkson, W. Liu, K. Albright, and M. W. Pariza, 1994, J. Nutr. 124: 694–701).

The method of the present invention may take other forms. For example, the CLA can be administered to an animal in a pharmaceutical or veterinary composition, such as tablets, capsules, solutions or emulsions, containing safe and effective doses of the CLA.

The animal feeds and pharmaceutical or veterinary compositions for use in the method of the present invention are those containing the active forms of the free conjugated linoleic acids (CLA), especially 9,11-octadecadienoic acid and 10,12-octadecadienoic acid or mixtures thereof in combination with a conventional animal feed, human food supplement, or an approved pharmaceutical diluent.

The active forms of CLA include, in addition to the free acids the active isomers of CLA; non-toxic salts thereof; active esters and other active chemical derivatives thereof; and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987). However, animal feeds containing CLA, or its non-toxic derivatives, such as the sodium and potassium salts or active esters, as an additive in combination with conventional animal feeds or human foods are believed to be novel.

The preferred method of synthesizing CLA is that described in Example 1. However, CLA may also be prepared from linoleic acid by the action of a linoleic acid isomerase from a harmless microorganism, such as the Rumen bacterium *Butyrivibrio fibrisolvens*. Harmless microorganisms such as *Lactobacillus reuteri* in the intestinal tracts of rats and other monogastric animals may also convert linoleic acid to CLA (S. F. Chin, J. M. Storkson, W. Liu, K. Albright and M. W. Pariza, 1994, J. Nutr. 124; 694–701).

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c9,c12) would be expected. However, of the four isomers, c9,t11- and t10,c12-isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The exact amount of CLA to be administered, of course, depends upon the animal, the form of CLA employed, and the route of administration. However, generally it will be an amount ranging from about 0.001 g/kg about 1 g/kg of the animals body weight.

Generally, the amount employed of CLA employed as a pharmaceutical for humans will range from about 1,000 parts per million (ppm) to about 10,000 ppm of CLA of the human's diet. However, the upper limit of the amount to be employed is not critical because CLA is relatively non-toxic and it is a normal constituent of the human diet (including human breast milk).

The preferred pharmaceutical and veterinary compositions of CLA contain the non-toxic sodium or potassium salt of CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

The amount of CLA to be added to an animal's feed to reduce Apolipoprotein can range from 0.01% to 2.0% or more by weight of the animal's or human's food. It can be added to the food by adding either relatively pure CLA to the food or by adding by-products, such as the fat of an animal which was fed CLA, to the food.

An especially preferred composition for use in humans might be a water in oil fat emulsion, such as Intralipid® (Baxter); Liposyn® (Abbott); Nutrilipid® (McGaw); or SoyaCal® (Alpha Therapeutic), in which about 0.5% to about 2% (preferably 1%) by weight of the oil has been replaced by CLA. These fat emulsions all contain emulsified fat particles of about 0.33–0.5 μm in diameter. In addition about 10% to 20% of the oils which are a mixture of neutral triglycerides of principally unsaturated fatty acids, the emulsions contain Water for Injection USP as a diluent, egg phosphatides (1–2%) as an emulsifying agent and glycerin (2–3%) to adjust toxicity. These emulsions can be infused intravenously to patients requiring parenteral nutrition.

Another preferred composition is a baby formula, in which about 0.5% to about 2% by weight (preferably 0.5%) by weight of the fat content has been replaced by a like amount of CLA or to which 0.5 to about 2% by weight has been added.

It will be readily apparent to those skilled in the art that a number of modifications or changes may be made without departing from the spirit and scope of the present invention. Therefore, the invention is only to be limited by the claims.

We claim:

1. A method of reducing secretion of Apolipoprotein B from an animal cell, the method comprising the step of exposing the cell to a compound selected from the group consisting of 9,11-octadecadienoic acid, 10,12-octadecadienoic acid, mixtures thereof, active esters and non-toxic salts thereof, in an amount effective to reduce the secretion of Apolipoprotein B from the cell.

2. A method as claimed in claim 1 wherein the cell is a human cell.

3. A method as claimed in claim 2 wherein the cell is a human hepatocyte.

4. A method of reducing apolipoprotein B secretion in an animal, the method comprising the step of administering to the animal a safe amount of a compound selected from the group consisting of 9,11-octadecadienoic acid, 10,12-octadecadienoic acid, mixtures thereof, active esters and non-toxic salts thereof which is effective to reduce the serum level of apolipoprotein B in the animal.

5. The method of claim 4 in which the amount of the compound administered is about 0.001 g/kg to about 1 g/kg of the animal's body weight.

6. A method of modifying an animal feed, formula or supplement so that it reduces serum Apolipoprotein B level of an animal to which it is fed, which comprises adding to said animal feed, formula or supplement a safe amount of a compound selected from the group consisting of 9,11-octadecadienoic acid, 10,12-octadecadienoic acid, mixtures thereof, active esters and non-toxic salts thereof, which when the feed is consumed by the animal will be effective to reduce the serum level of Apolipoprotein B in the animal.

7. The method of claim 6 in which the animal is a mammal.

8. A method of reducing secretion of Apolipoprotein B from an animal cell, the method comprising the step of exposing the cell in vitro to a compound selected from the group consisting of 9,11-octadecadienoic acid, 10,12-octadecadienoic acid, mixtures thereof, active esters and non-toxic salts thereof, in an amount effective to reduce the secretion of Apolipoprotein B from the cell.

9. A method as claimed in claim 8 wherein the cell is a human cell.

10. A method as claimed in claim 9 herein the cell is a human hepatocyte.

* * * * *